(12) United States Patent
Grela et al.

(10) Patent No.: US 9,221,042 B2
(45) Date of Patent: Dec. 29, 2015

(54) METAL COMPLEXES, ESPECIALLY THE RUTHENIUM COMPLEXES, AND USE THEREOF

(71) Applicant: Apeiron Synthesis S.A., Wroclaw (PL)

(72) Inventors: Karol Grela, Warsaw (PL); Christian Torborg, Alfeld (DE); Grzegorz Szczepaniak, Warsaw (PL); Adam Zielinski, Warsaw (PL)

(73) Assignee: APEIRON SYNTHESIS S.A., Wroclaw (PL)

( * ) Notice: Subject to any disclaimer, the term of this patent is extended or adjusted under 35 U.S.C. 154(b) by 0 days.

(21) Appl. No.: 14/421,752

(22) PCT Filed: Aug. 14, 2013

(86) PCT No.: PCT/EP2013/067027
§ 371 (c)(1),
(2) Date: Feb. 13, 2015

(87) PCT Pub. No.: WO2014/027040
PCT Pub. Date: Feb. 20, 2014

(65) Prior Publication Data
US 2015/0217283 A1 Aug. 6, 2015

(30) Foreign Application Priority Data

Aug. 16, 2012 (PL) .......................... 400397

(51) Int. Cl.
| | | |
|---|---|---|
| *C07F 15/00* | (2006.01) | |
| *B01J 31/12* | (2006.01) | |
| *B01J 31/22* | (2006.01) | |
| *C07C 6/04* | (2006.01) | |
| *C07C 67/333* | (2006.01) | |
| *C07F 7/18* | (2006.01) | |
| *C07D 207/48* | (2006.01) | |
| *C07D 209/30* | (2006.01) | |
| *C07D 211/96* | (2006.01) | |
| *C07D 307/28* | (2006.01) | |
| *C08F 132/08* | (2006.01) | |

(52) U.S. Cl.
CPC .......... *B01J 31/2295* (2013.01); *B01J 31/2273* (2013.01); *B01J 31/2278* (2013.01); *C07C 6/04* (2013.01); *C07C 67/333* (2013.01); *C07D 207/48* (2013.01); *C07D 209/30* (2013.01); *C07D 211/96* (2013.01); *C07D 307/28* (2013.01); *C07F 7/1852* (2013.01); *C07F 7/1892* (2013.01); *C07F 15/0046* (2013.01); *C08F 132/08* (2013.01); *B01J 2231/54* (2013.01); *B01J 2531/821* (2013.01); *B01J 2531/825* (2013.01); *C07B 2200/09* (2013.01); *C07C 2101/10* (2013.01); *C07C 2531/22* (2013.01); *C07C 2531/24* (2013.01)

(58) Field of Classification Search
USPC ................................ 548/103; 546/2; 502/155
See application file for complete search history.

(56) References Cited

U.S. PATENT DOCUMENTS 7,238,816 B2 * 7/2007 Puentener et al. ............ 549/271

FOREIGN PATENT DOCUMENTS

| EP | 1 971 616 A1 | 9/2008 |
|---|---|---|
| WO | 2006/111491 A1 | 10/2006 |
| WO | 2008/155338 A2 | 12/2008 |
| WO | 2010/037550 A1 | 4/2010 |
| WO | 2011/117571 A1 | 9/2014 |

OTHER PUBLICATIONS

Monsaert, S. et al.: Indenylidene complexes of Rhuthenium bearing NHC ligands-structure elucidation and performance as catalysts for olefin metathesis. Eur. J. Org. Chem., pp. 655-665, 2009.*

(Continued)

*Primary Examiner* — Charanjit Aulakh
(74) *Attorney, Agent, or Firm* — Seed IP Law Group PLLC

(57) ABSTRACT

Described herein are novel metal complexes, especially ruthenium complexes, represented by the formula (1):

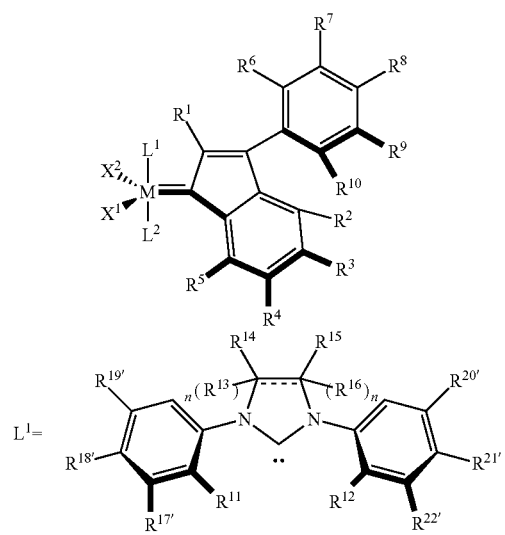

wherein $L^1$ is a N-heterocyclic carbene ligand, $L^2$ is a neutral phosphine ligand, preferably tricyclohexyl-phosphine, and process of catalyzing olefin metathesis reactions, especially tetra-substituted olefin metathesis reactions.

10 Claims, 2 Drawing Sheets

(56) References Cited

OTHER PUBLICATIONS

Sashuk et al., "[(NHC)(NHC$_{ewg}$)RuCl$_2$(CHPh)] Complexes with Modified NHC$_{ewg}$ Ligands for Efficient Ring-Closing Metathesis Leading to Tetrasubstituted Olefins," *Chem. Eur. J. 16*:3983-3993, 2010.

Savka et al., "A hexahydro-*s*-indacene based NHC ligand for olefin metathesis catalysts," *Journal of Organometallic Chemistry 710*:68-74, 2012.

Scholl et al., "Synthesis and Activity of a New Generation of Ruthenium-Based Olefin Metathesis Catalysts Coordinated with 1,3-Dimesityl-4,5-dihydroimidazol-2-ylidene Ligands," *Organic Letters 1*(6):953-956, 1999.

Schrock., "Recent advances in olefin metathesis by molybdenum and tungsten imido alkylidene complexes," *Journal of Molecular Catalysis A: Chemical 213*:21-30, 2004.

Stewart et al., "Highly Efficient Ruthenium Catalysts for the Formation of Tetrasubstituted Olefins via Ring-Closing Metathesis," *Organic Letters 9*(8):1589-1592, 2007.

Torborg et al., "Stable ruthenium indenylidene complexes with a sterically reduced NHC ligand," *Chem. Commun. 49*:3188-3190, 2013.

Weatherhead et al., "Tandem Catalytic Asymmetric Ring-Opening Metathesis/Ring-Closing Metathesis," *J. Am. Chem. Soc. 122*:1828-1829, 2000.

\* cited by examiner

METAL COMPLEXES, ESPECIALLY THE RUTHENIUM COMPLEXES, AND USE THEREOF

FIELD OF THE INVENTION

The invention relates to novel metal complexes, especially to the ruthenium complexes, being useful as (pre)catalysts, as well as to their use in the olefin metathesis reaction. This invention finds its application in the broadly understood organic synthesis.

BACKGROUND OF THE INVENTION

Significant advances have been achieved in the uses of olefin metathesis for organic synthesis recently (*Handbook of Metathesis*, Vols. I-III, Grubbs, R. H., ed.; Wiley-VCH, 2003; and Michalak, M.; Gułajski, Ł.; Grela, K. "*Alkene Metathesis*" in: *Science of Synthesis: Houben-Weyl Methods of Molecular Transformations*, Vol. 47a *Alkenes*, de Meijere, A., ed.; Georg Thieme Verlag KG, 2010, pp. 327-438).

The literature relevant to catalysis proposes describing the ruthenium-containing catalysts for olefin metathesis as (pre)catalysts, since it is not proven whether the compounds, that under certain circumstances would catalyse the olefin metathesis, are identical with the active substances participating in the metathesis reaction or not (see, R. R. Schrock, *J. Mol. Catal. A: Chem.* 213, 21 (2004)). Because of that, the inventors use the term (pre)catalyst in this specification, wishing not to be bound by any particular theory describing the metathesis reaction mechanisms.

Several ruthenium carbene complexes are known in the state of the art, that have both a high activity in various variants of the metathesis reactions as well as a broad tolerability for functional groups. The above-mentioned combination of properties is a prerequisite of catalysts of such type in the organic synthesis. Exemplary complexes of this type are the (pre)catalysts (A), (B) and (C) (A—S. P. Nolan, *Organometallics*, 18, 25, (1999), B—R. H. Grubbs, *Org. Lett.* 1, 9, (1999), C—A. H. Hoveyda *J. Am. Chem. Soc.* 122, 34, (2000)).

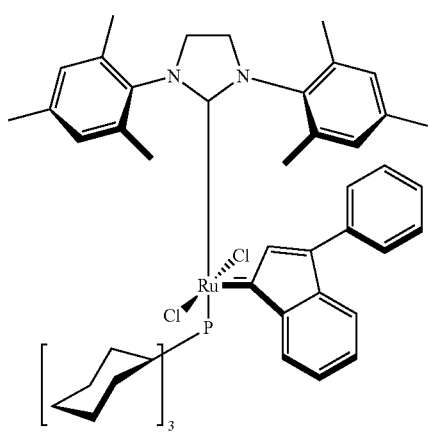

A

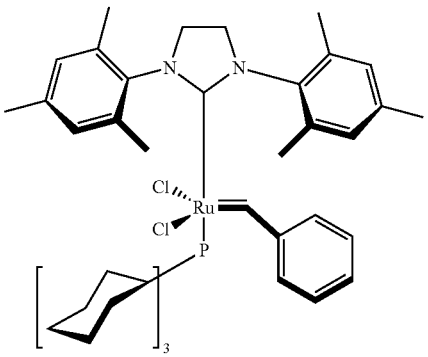

B

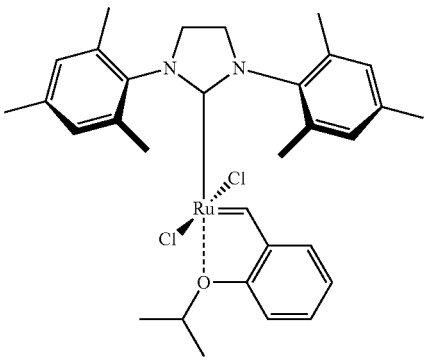

C

However, there are few complexes known that effectively promote formation of tetra-substituted olefins. Examples of this type of complexes include the (pre)catalysts (D), (E), and (F) (D and E—R. H. Grubbs, *Org. Lett.*, 9, 8, (2007); F—H. Plenio, *Chem. Eur. J.*, 16, 41, (2010)).

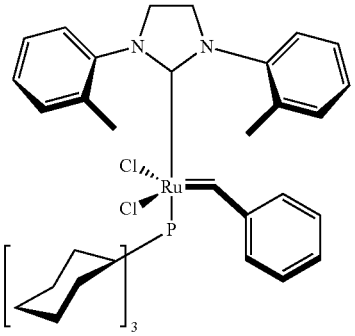

D

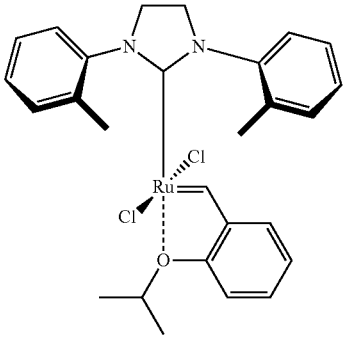

E

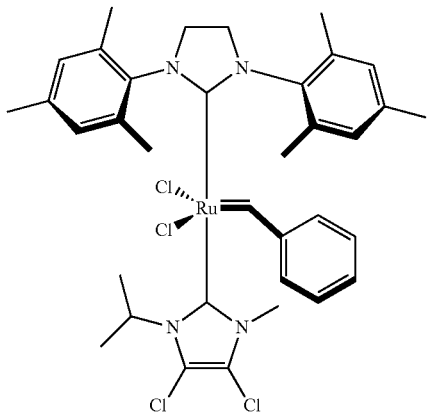

F

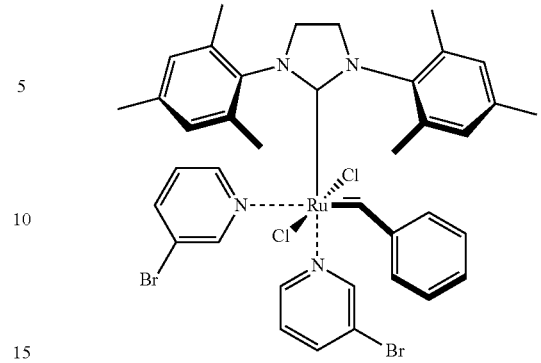

The major drawback of the complexes (D) and (E) is their limited stability both in the solid state and in the solution, what poses problems related to their storage and limits their effectiveness in the metathesis reactions. The complexes such as (F) are much more stable and effective in metathesis reactions, but their preparation requires using the corresponding (pre)catalyst containing pyridinium ligands (the so-called third generation catalyst) as a substrate, as well as the compounds containing silver atom in their structure, what significantly extends the synthetic pathway and drastically increases the synthesis costs.

The third-generation complexes, such as (G) and (H), are the useful (pre)catalysts for metathesis of olefins. They are characterised by rapid initiation as well as high effectiveness and selectivity in some ring-opening metathetic polymerisation reactions (ROMP).

G

In turn, the complexes containing an indenylidene ligand in their structure, such as, for example, the complex (G), are very stable both in the solid state and in the solution. There are no known complexes in the state of the art that would contain the indenylidene ligand and the o-tolyl ligand.

The organometallic complexes of ruthenium containing the o-tolyl ligand are described in the patent documents Nos. EP 1971616 A, U.S. Pat. No. 8,008,224 B2, JP 2009519947 A, KR 20080103961 A, and CN 101460513.

The organometallic complexes of ruthenium, being the third-generation (pre)catalysts, containing the o-tolyl ligand and a pyridine molecule, are described in the international patent application No. WO 2007/075427 A1.

DISCLOSURE OF THE INVENTION

Figure 1:
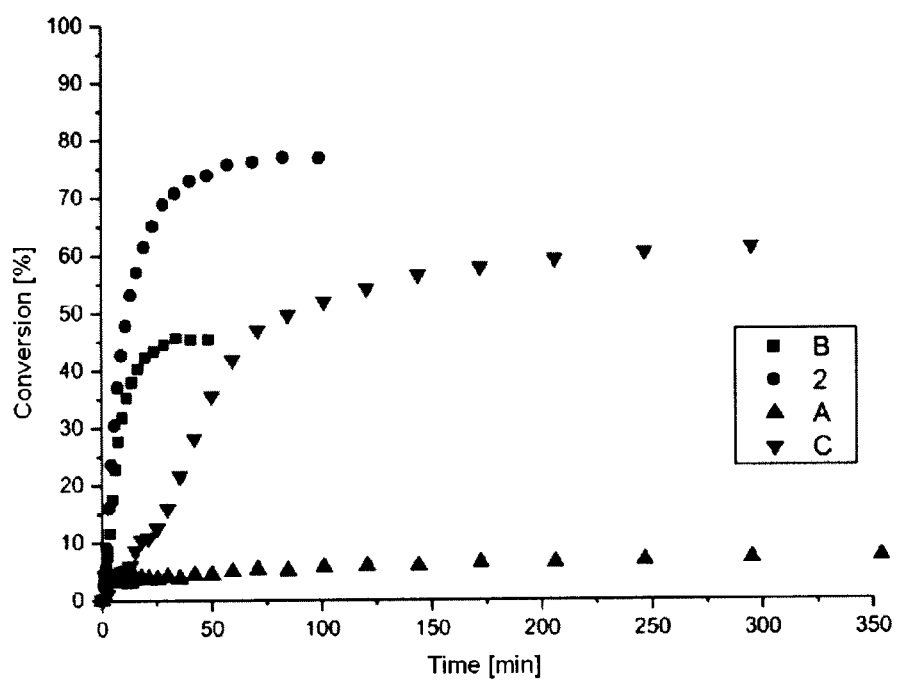
FIG. 1 shows the reaction progress for cyclisation of diethyl di(allylmethyl)malonate in the presence of various catalysts.
Figure 1:
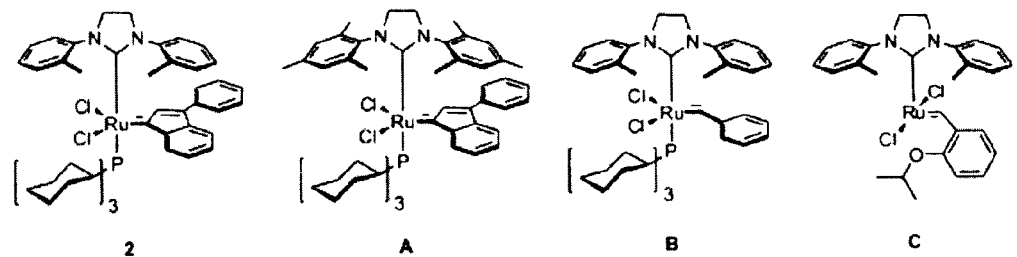

It was found that the novel metal complexes, especially ruthenium complexes, represented by the formula (1):

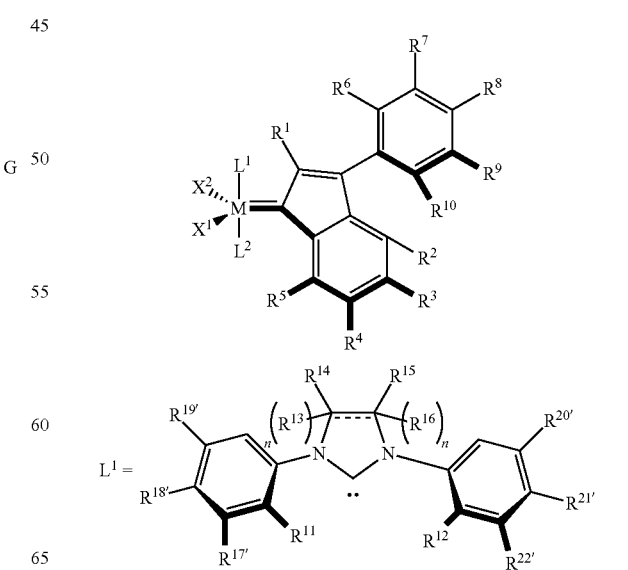

wherein L¹ is a N-heterocyclic carbene ligand, L² is a neutral phosphine ligand, preferably tricyclohexylphosphine, feature a stability significantly higher both in the solution and in the solid state and catalyse the tetra-substituted olefin metathesis reactions more effectively than the complex (D). Besides, it was unexpectedly found that it was possible to replace the neutral phosphine ligand L² with a nitrogen ligand such as pyridine. As a result of such a replacement, a third generation (pre)catalyst is obtained from a second generation (pre)catalyst. The third generation (pre)catalysts of the formula (1) are characterised by a high rate of initiation in many metathesis reactions, including the ROMP-type polymerisation. It was also unexpectedly found that, in spite of a significantly higher stability, the complexes of the formula (1) initiate the metathesis reactions at rates superior or close to the rates of reactions promoted by the complexes (A) and (D).

The complexes of the formula (1) according to the invention find their application in a broad range of reactions. Both numerous ring-closing metathesis (RCM) reactions, as well as homometathesis, cross metathesis (CM) and metathesis of the "alkene-alkynen" (ene-yne) type, isomerisation reactions and ring-opening metathesis polymerisation (ROMP) reaction can be carried out to a good result. The main advantage of lo the complexes of the formula (1) is their high activity in the reactions of metathetic ring closing, in which tetra-substituted olefins are obtained. Besides, the complexes of the formula (1) are highly stable in the solid state and in the solution, and their synthesis may be carried out in an efficient way from inexpensive, commercially available substrates.

DETAILED DESCRIPTION OF THE INVENTION

The invention relates to novel metal complexes of the formula (1), containing a N-heterocyclic carbene ligand L¹ in their structure:

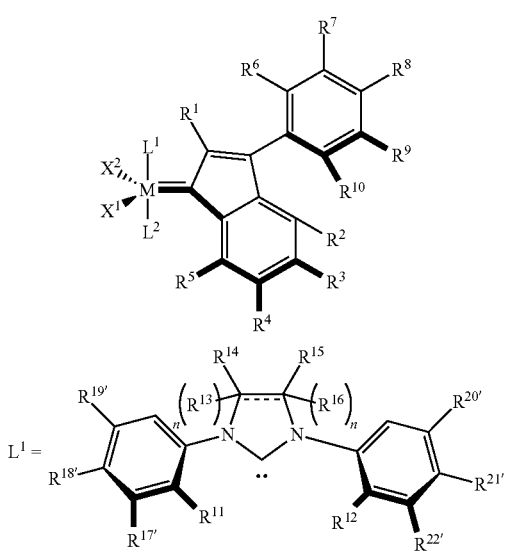

wherein:
M is ruthenium or osmium;
L¹ is a N-heterocyclic carbene ligand, where $R^{11}$, $R^{12}$, $R^{17'}$, $R^{18'}$, $R^{19'}$, $R^{20'}$, $R^{21'}$, and $R^{22'}$ are independently hydrogen, $C_1$-$C_{25}$ alkyl, $C_1$-$C_{25}$ alkoxy, or $C_2$-$C_{25}$ alkenyl, where $R^{11}$ and $R^{12}$ may be joined together to form a cyclic $C_4$-$C_{16}$ system, optionally the substituents $R^{11}$, $R^{17'}$, $R^{18'}$, $R^{19'}$ and/or the substituents $R^{12}$, $R^{20'}$, $R^{21'}$, $R^{22'}$ may be joined together to form a substituted or unsubstituted cyclic $C_4$-$C_{10}$ or polycyclic $C_4$-$C_{12}$ system;
$R^{13}$, $R^{14}$, $R^{15}$, and $R^{16}$ are independently hydrogen or $C_1$-$C_{25}$ alkyl, where $R^{13}$ and/or $R^{14}$ may be joined to $R^{15}$ and/or $R^{16}$, to form a cyclic system;
n is 0 or 1.
The value of n=0 means that there are no substituents $R^{13}$ and $R^{16}$ in the formula (1), and the bond depicted as ═══ represents a double bond;
L² is a neutral ligand;
X¹ and X² are independently an anionic ligand;
$R^1$, $R^2$, $R^3$, $R^4$, $R^5$, $R^6$, $R^7$, $R^8$, $R^9$, and $R^{10}$ are independently hydrogen, halogen, $C_1$-$C_{25}$ alkyl, $C_1$-$C_{25}$ alkylamino, $C_1$-$C_{25}$ alkylammonium, $C_1$-$C_{25}$ perfluoroalkyl, $C_2$-$C_{25}$ alkenyl, $C_3$-$C_7$ cycloalkyl, $C_3$-$C_{25}$ cycloalkenyl, $C_2$-$C_{25}$ alkynyl, $C_3$-$C_{25}$ cycloalkynyl, $C_1$-$C_{25}$ alkoxy, $C_5$-$C_{24}$ aryl, $C_5$-$C_{20}$ heteroaryl, $C_3$-$C_{12}$ heterocyclyl, thioether (—SR'), ester (—COOR'), amide (—CONR'₂) sulphone (—SO₂R'), sulphonamide (—SO₂NR'₂), or ketone (—COR'), in which groups R' is $C_1$-$C_5$ alkyl, $C_1$-$C_5$ perfluoroalkyl, $C_5$-$C_{24}$ aryl, $C_5$-$C_{24}$ perfluoroaryl;

In a preferred embodiment,
M is ruthenium;
L¹ is a N-heterocyclic carbene ligand, where $R^{11}$, $R^{12}$, $R^{17'}$, $R^{18'}$, $R^{19'}$, $R^{20'}$, $R^{21'}$, and $R^{22'}$ are independently hydrogen, $C_1$-$C_{25}$ alkyl, $C_1$-$C_{25}$ alkoxy, or $C_2$-$C_{25}$ alkenyl, where $R^{11}$ and $R^{12}$ may be joined together to form a cyclic $C_4$-$C_{16}$ system, optionally the substituents $R^{11}$, $R^{17'}$, $R^{18'}$, $R^{19'}$ and/or the substituents $R^{12}$, $R^{20'}$, $R^{21'}$, $R^{22'}$ may be joined together to form a substituted or unsubstituted cyclic $C_4$-$C_{10}$ or polycyclic $C_4$-$C_{12}$ system;
$R^{13}$, $R^{14}$, $R^{15}$, $R^{16}$ are independently hydrogen or $C_1$-$C_{25}$ alkyl, where $R^{13}$ and/or $R^{14}$ may be joined to $R^{15}$ and/or $R^{16}$, to form a cyclic system;
n is 0 or 1.
L² is described by the formula $P(R^{17})(R^{18})(R^{19})$, where $R^{17}$, $R^{18}$ and $R^{19}$ are independently $C_1$-$C_{12}$ alkyl, $C_1$-$C_{12}$ alkoxy, $C_3$-$C_{12}$ cycloalkyl, $C_5$-$C_{12}$ aryl, $C_5$-$C_{12}$ aryloxy, or $C_5$-$C_{12}$ heteroaryl, where two substituents selected from $R^{17}$, $R^{18}$ and $R^{19}$ may be joined together to form a cyclic or polycyclic system; or also L² is selected from the group comprising nitrogen-containing heterocycles, such as 1,2,3-triazole, 1,3,4-triazole, pyridine, 4-(N,N-dimethylamino)pyridine (DMAP), piperidine, morpholine, thiomorpholine, pyridazine, pyrimidine, pyrazine, piperazine, 1,2,3-triazine, 1,2,4-triazine, 1,3,5-triazine, quinoline, isoquinoline, quinuclidine, phthalazine, indoline, thiazole, benzothiazole, benzimidazole, purine, 1,8-naphthyridine, quinoxaline, pteridine, carbazole, phenazine, carboline, isothiazole, tetrazole, quinine, cinchonine, quinidine, cinchonidine, 1,8-diazabicyclo[5.4.0]undec-7-ene (DBU), 1,4-diazabicyclo[2.2.2]octane (DABCO), 1,5-diazabicyclo [4.3.0]non-5-ene (DBN), phenanthroline, and bipyridyl (as a single isomer or as a mixture of isomers), that are optionally substituted with at least one $C_1$-$C_{12}$ alkyl, $C_1$-$C_{12}$ perhaloalkyl, $C_1$-$C_{12}$ alkoxy, amino, cyano, alkoxy, or halogen(s).
X¹ and X² are independently halogen, —CN, —SCN, —OR²⁰, —SR²⁰, —O(C═O)R²⁰, —O(SO₂)R²⁰, —OSiR₃²⁰, where R²⁰ is $C_1$-$C_{16}$ alkyl, $C_3$-$C_{16}$ cycloalkyl, $C_2$-$C_{12}$ alkenyl, or $C_5$-$C_{25}$ aryl, that is optionally substituted with at least one $C_1$-$C_{12}$ alkyl, $C_1$-$C_{12}$ perhaloalkyl, $C_1$-$C_{12}$ alkoxy, or halogen(s);
$R^1$, $R^2$, $R^3$, $R^4$, $R^5$, $R^6$, $R^7$, $R^8$, $R^9$, $R^{10}$ are independently hydrogen, halogen, $C_1$-$C_{25}$ alkyl, $C_1$-$C_{25}$ alkylamino, $C_1$-$C_{25}$ alkylammonium, $C_1$-$C_{25}$ perfluoroalkyl, $C_2$-$C_{25}$ alkenyl, $C_3$-$C_7$ cycloalkyl, $C_3$-$C_{25}$ cycloalkenyl, $C_2$-$C_{25}$ alkynyl, $C_3$-$C_{25}$ cycloalkynyl, $C_1$-$C_{25}$ alkoxy, $C_5$-$C_{24}$ aryl, $C_5$-$C_{20}$ heteroaryl, $C_{3-12}$ heterocyclyl, thioether (—SR'), ester (—COOR'), amide (—CONR'$_2$), sulphone (—SO$_2$R'), sulphonamide (—SO$_2$NR'$_2$), or ketone (—COR'), in which groups R' is $C_1$-$C_5$ alkyl, $C_1$-$C_5$ perfluoroalkyl, $C_5$-$C_{24}$ aryl, or $C_5$-$C_{24}$ perfluoroaryl;

In another preferred embodiment,

M is ruthenium;

$L^1$ is a N-heterocyclic carbene ligand, where $R^{11}$, $R^{12}$, $R^{17'}$, $R^{18'}$, $R^{19'}$, $R^{20'}$, $R^{21'}$ and $R^{22'}$ are independently hydrogen, $C_1$-$C_{25}$ alkyl, $C_1$-$C_{25}$ alkoxy, or $C_2$-$C_{25}$ alkenyl, where $R^{11}$ and $R^{12}$ may be joined together to form a cyclic $C_4$-$C_{16}$ system, optionally the substituents $R^{11}$, $R^{17'}$, $R^{18'}$, $R^{19'}$ and/or the substituents $R^{12}$, $R^{20'}$, $R^{21'}$, $R^{22'}$ may be joined together to form a substituted or unsubstituted cyclic $C_4$-$C_{10}$ or polycyclic $C_4$-$C_{12}$ system;

$R^{13}$, $R^{14}$, $R^{15}$, $R^{16}$ are independently hydrogen or $C_1$-$C_{25}$ alkyl, where $R^{13}$ and/or $R^{14}$ may be joined to $R^{15}$ and/or $R^{16}$, to form a cyclic system;

n is 0 or 1.

$L^2$ is triphenylphosphine, tricyclohexylphosphine, pyridine or 3-bromopyridine;

$X^1$ and $X^2$ are independently halogen;

$R^1$, $R^2$, $R^3$, $R^4$, $R^5$, $R^6$, $R^7$, $R^8$, $R^9$, $R^{10}$ are independently hydrogen, halogen, $C_1$-$C_{16}$ alkyl, $C_1$-$C_{16}$ alkoxy, thioether (—SR'), ester (—COOR'), or ketone (—COR'), in which groups R' is $C_1$-$C_5$ alkyl, $C_1$-$C_5$ perfluoroalkyl, $C_5$-$C_{24}$ aryl, or $C_5$-$C_{24}$ perfluoroaryl.

Preferably $L^1$ is a N-heterocyclic carbene ligand, where $R^{11}$ and $R^{12}$ are methyl, each $R^{17'}$, $R^{18'}$, $R^{19'}$, $R^{20'}$, $R^{21'}$ and $R^{22'}$ is independently hydrogen or methyl, and n is 0 or 1.

Preferably $L^2$ is triphenylphosphine, tricyclohexylphosphine, pyridine or 3-bromopyridine.

Preferably $X^1$ and $X^2$ are chloro.

$R^1$, $R^2$, $R^3$, $R^4$, $R^5$, $R^6$, $R^7$, $R^8$, $R^9$, $R^{10}$ are independently hydrogen, halogen or $C_1$-$C_6$ alkoxy.

Preferably each $R^{13}$, $R^{14}$, $R^{15}$, and $R^{16}$ is independently is hydrogen or methyl.

Preferably the metal complex according to the invention has a structural formula selected from the following formulae (2), (3), (4), (5) and (6).

2

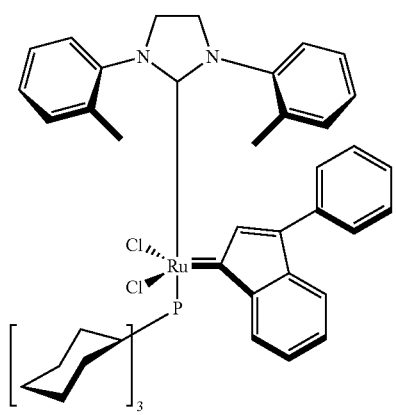

3

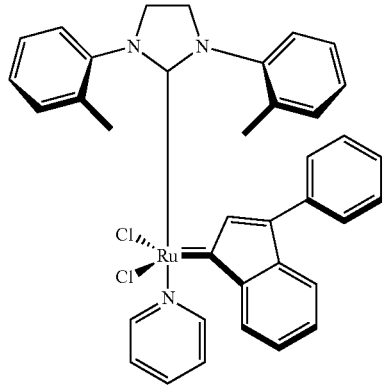

4

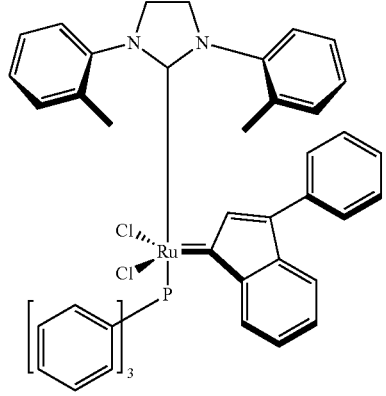

5

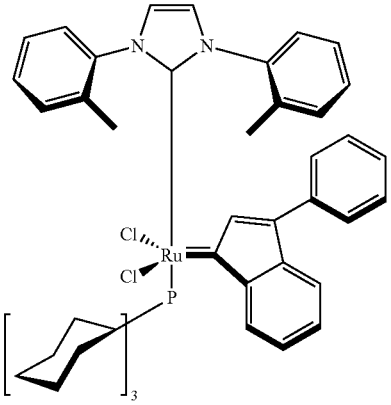

6

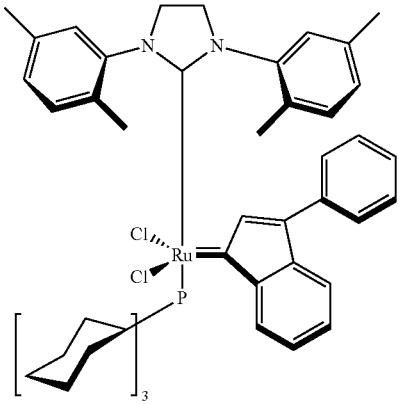

The invention is related also to use of one or more complexes of ruthenium, as defined above by the formula (1), as a (pre)catalyst in the olefin metathesis reaction.

Preferably, the ruthenium complex of the formula (1) is used as a (pre)catalyst in the ring-closing metathesis (RCM), homometathesis, cross metathesis (CM), "alkene-alkyne" (ene-yne) type metathesis, isomerisation, or ROMP-type polymerisation reactions.

Preferably, the ruthenium complex of the formula (1) is used as a (pre)catalyst in the metathetic polymerisation reaction with opening of ring of dicyclopentadiene or norbornene.

Preferably, a solution of the (pre)catalyst of the formula (1) in an organic solvent is added to the reaction mixture in a period of from 1 minute to 24 hours. Preferably, the solution of the (pre)catalyst is prepared in the same solvent in which the metathesis reaction is carried out. Alternatively, the reaction using the (pre)catalyst of the formula (1) is carried out without using any solvent.

The complexes of the formula (1) are used also for the synthesis of other complex compounds being the (pre)catalysts for olefin metathesis reactions, including the Hoveyda-Grubbs type (pre)catalysts.

The term "halogen" means an atom of element selected from F, Cl, Br, I.

The term "carbene" means a moiety containing a neutral carbon atom having the valence number equal to two, as well as two non-paired valence electrons. The term "carbene" covers also the carbene analogues in which the carbon atom is replaced with an atom of another chemical element, such as boron, silicon, germanium, tin, lead, nitrogen, phosphor, sulphur, selenium, and tellurium.

The terms "alkyl group" and "alkyl" refer to a saturated, straight-chain or branched-chain hydrocarbon substituent s having the indicated number of carbon atoms. Examples of straight-chain alkyl substituent are methyl, ethyl, n-propyl, n-butyl, n-pentyl, n-hexyl, n-heptyl, n-octyl, n-nonyl, and n-decyl. The representative branched-chain $C_3$-$C_{10}$ alkyl substituents comprise isopropyl, sec-butyl, isobutyl, tert-butyl, isopentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, 3,3-dimethylheptyl, and the like.

The term "alkoxy" refers to an alkyl substituent, as defined above, joined via oxygen atom.

The term "perhaloalkyl" means alkyl, as defined above, in which all hydrogen atoms are replaced with identical or different halogen atoms.

The term "cycloalkyl" refers to a saturated mono- or polycyclic hydrocarbon substituent having the indicated number of carbon atoms. The examples of cycloalkyl substituent are cyclopropyl, cyclobutyl, cyclopentyl, cyclohexyl, cycloheptyl, cyclooctyl, cyclononyl, cyclodecyl, and the like.

The term "alkenyl" refers to a straight-chain or branched-chain non-cyclic hydrocarbon substituent having the indicated number of carbon atoms and containing at least one carbon-carbon double bond. The examples of alkenyl substituent are vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl, and the like.

The term "cycloalkenyl" refers to a mono- or polycyclic hydrocarbon substituent having the indicated number of carbon atoms and containing at least one carbon-carbon double bond. The examples of cycloalkenyl substituent are cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodekadienyl, and the like.

The term "alkynyl" refers to a straight-chain or branched-chain, non-cyclic hydrocarbon substituent having the indicated number of carbon atoms and containing at least one carbon-carbon triple bond. The examples of alkynyl substituent are acetylenyl (ethynyl), propynyl, 1-butynyl, 2-butynyl, 1-pentynyl, 2-pentynyl, 3-methyl-1-butynyl, 4-pentynyl, 1-hexynyl, 2-hexynyl, 5-hexynyl, and the like.

The term "cycloalkynyl" refers to a mono- or polycyclic hydrocarbon substituent having the indicated number of carbon atoms and containing at least one carbon-carbon triple bond. The examples of cycloalkynyl substituent are cyclohexynyl, cycloheptynyl, cyclooctynyl, and the like.

The term "aryl" refers to an aromatic mono- or polycyclic hydrocarbon substituent having the indicated number of carbon atoms. The examples of aryl substituent are phenyl, tolyl, xylyl, naphthyl, and the like.

The term "heteroaryl" refers to an aromatic mono- or polycyclic hydrocarbon substituent having the indicated number of carbon atoms, in which at least one carbon atom was replaced with a heteroatom selected from O, N and S. The examples of heteroaryl substituent are furyl, thienyl, imidazolyl, oxazolyl, thiazolyl, isoxazolyl, triazolyl, oxadiazolyl, thiadiazolyl, tetrazolyl, pyridyl, pyrimidyl, triazinyl, indolyl, benzo[b]furyl, benzo[b]thienyl, indazolyl, benzimidazolyl, azaindolyl, quinolyl, isoquinolyl, carbazolyl, and the like.

The term "heterocyclyl" refers to a saturated or partially unsaturated, mono- or polycyclic hydrocarbon substituent, having the indicated number of carbon atoms, in which at least one carbon atom was replaced with a heteroatom selected from O, N and S. The examples of heterocyclyl substituent are furyl, thiophenyl, pyrrolyl, oxazolyl, imidazolyl, thiazolyl, isoxazolyl, pyrazolyl, isothiazolyl, triazinyl, pyrrolidinonyl, pyrrolidinyl, hydantoinyl, oxiranyl, oxetanyl, tetrahydrofuryl, tetrahydrothiophenyl, quinolinyl, isoquinolinyl, chromonyl, coumarinyl, indolyl, indolizinyl, benzo[b]furyl, benzo[b]thiophenyl, indazolyl, purinyl, 4H-quinolizinyl, isoquinolyl, quinolyl, phthalazinyl, naphthyridinyl, carbazolyl, β-carbolinyl, and the like.

The term "neutral ligand" refers to a substituent having no net charge, able to co-ordinate with a metallic centre (ruthenium atom). The examples of such ligands may be amines, phosphines and oxides thereof, alkyl and aryl phosphites and phosphates, arsines and oxides thereof, ethers, alkyl and aryl sulphides, co-ordinated hydrocarbons, alkyl and aryl halides.

The term "anionic ligand" refers to a substituent able to co-ordinate with a metallic centre (ruthenium atom), having net charge able to partially or completely compensate the charge of the metallic centre. The examples of such ligands may be fluoride, chloride, bromide, iodide, cyanide, cyanate, and thiocyanate anions, carboxylic acid anions, alcoholates, phenolates, thiolates and thiophenolates, hydrocarbon anions having a delocalised charge (e.g., cyclopentadiene anion), (organo)sulphuric and (organo)phosphoric acid anions and anions of their esters (such as, e.g., anions of alkylsulphonic and arylsulphonic acids, anions of alkylphosphoric and arylphosphoric acids, anions of alkyl and aryl esters of sulphuric acid, anions of alkyl and aryl esters of phosphoric acids, anions of alkyl and aryl esters of alkylphosphoric and arylphosphoric acids).

The anionic ligands ($X^1$, $X^2$) and the neutral ligands ($L^1$, $L^2$, and, optionally, an analogous $L^3$) may be joined each other, to form multidentate ligands, for example: a bidentate ligand ($X^1 \smile X^2$), a tridentate ligand ($X^1 \smile X^2 \smile L^1$), a tetradentate ligand ($X^1 \smile X^2 \smile L^1 \smile L^2$), a bidentate ligand ($X^1 \smile L^1$), a tridentate ligand ($X^1 \smile L^1 \smile L^2$), a tetradentate ligand ($X^1 \smile L^1 \smile L^2 \smile L^3$), a bidentate ligand ($L^1 \smile L^2$), a tridentate ligand ($L^1 \smile L^2 \smile L^3$). The examples of such ligands are catecholate anion, acetylacetonate anion, and salicylaldehyde anion.

The term "indenylene" refers to an unsaturated hydrocarbon substituent having the structure of indene (benzocyclopentadiene).

Now the invention will be illustrated by the following examples that are intended to enable better understanding of the invention, but should by no means limit its scope.

The commercially available compounds (Sigma-Aldrich, Strem Chemicals, Apeiron Synthesis) were used in the reactions without additional purification. The reactions were carried out under the protective argon atmosphere in previously dried reaction flasks using the Schlenk technique, by using dry, de-oxygenated solvents, distilled under the protective argon atmosphere, over the drying agents; toluene, toluene -$d_8$, benzene-$d_6$ over potassium, dichloromethane, dichloromethane -$d_2$ over $CaH_2$. The reaction without using protective argon atmosphere were carried out using dichloromethane and toluene of HPLC grade (Sigma-Aldrich). The course of reaction was monitored by thin-layer chromatography (TLC), using silica gel plates with fluorescence indicator from Merck (Kieselgel 60 F254). The TLC plates were visualised using 254 nm UV light or using an aqueous $KMnO_4$ solution.

The separations on a chromatographic column by flash technique were carried out using silica gel (Merck silica gel 60, 230-400 mesh). The NMR spectra were recorded using Varian spectrometers: UnityPlus 200 MHz and INOVA 500 MHz.

The chemical shifts are reported in ppm relative to TMS ($\delta$=0 ppm) as a standard or relative to dichloromethane-$d_2$ ($\delta$=5.32 ppm) or relative to chloroform-$d_1$ ($\delta$=7.26 ppm).

Analysis of reaction mixtures was carried out by gas chromatography (GC) on a Clarus® 580 GC from PerkinElmer, using InterCap column 5MS/Sil having a length of 30 m and a diameter of 0.25 mm. The IR spectra were recorded using Perkin Elmer 2000. The MS analyses were carried out by electrospray ionisation (ESI) technique using a spectrometer Quattro LC. The combustion analyses were carried out in an analytical laboratory of the Institute of Organic Chemistry of the Polish Academy of Sciences.

Example I:

Synthesis of the (Pre)Catalyst [(oTol)RuCl$_2$(PCy$_3$)(Ind)] (Formula 2)

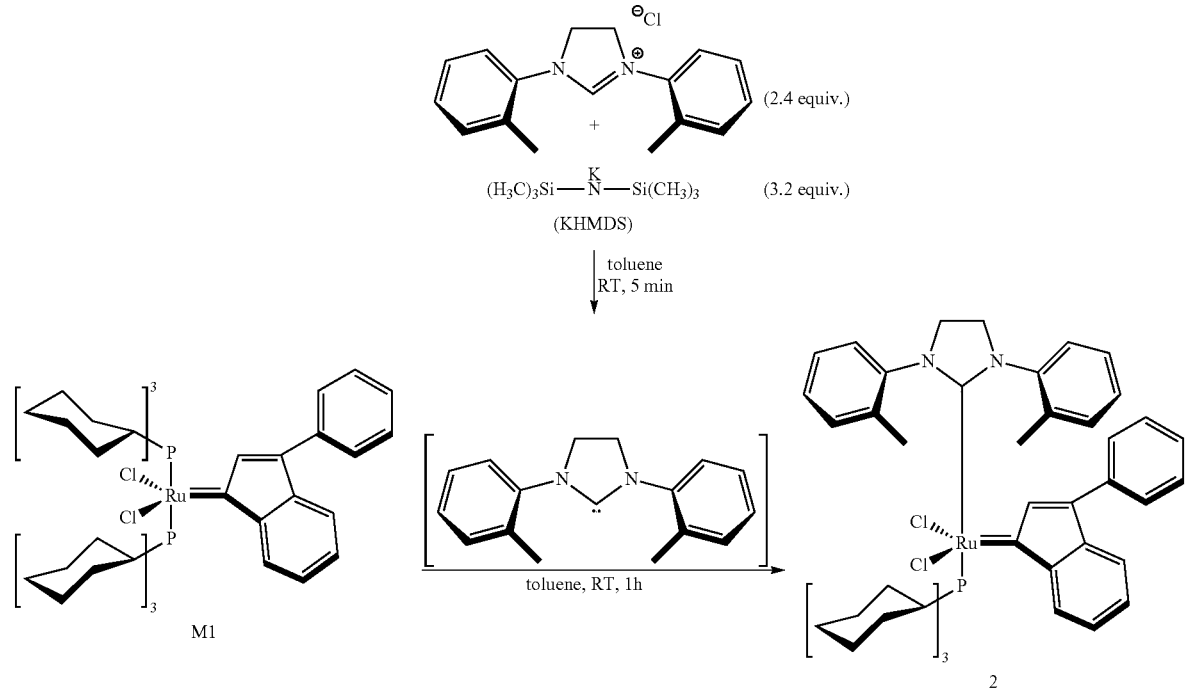

Using protective argon atmosphere, 500 mg (0.542 mmol) of the solid (pre)catalyst (M1) were placed in the Schlenk flask #1, followed by adding dry, deoxygenated toluene (40 ml). Using protective argon atmosphere, 374 mg (1.3 mmol, 2.4 equiv.) of 1,3-di-o-tolyl-4,5-dihydro-3H-imidazole chloride (the NHC salt) were placed in the Schlenk flask #2, followed by adding a KHMDS solution (1.73 mmol, 3.2 equiv.) in dry, deoxygenated toluene (10 ml). The reaction mixture was stirred at room temperature for 1-5 minutes, and then the so-obtained clear solution of free carbene was transferred via cannula to the Schlenk flask #1, using argon overpressure. The resulting reaction mixture was stirred at room temperature for 1 hour. From that moment on, all further operations were carried out without using protective argon atmosphere. The reaction mixture was concentrated in vacuo at a temperature of 30° C., and the obtained residue (10 ml)

was chromatographed over silica gel, using 4% of ethyl acetate in cyclohexane as an eluent.

Then the solvents were evaporated in vacuo at a temperature of 30° C., to yield the product as a film. n-Pentane was added to the purified product (5 ml), the resulting suspension was placed in an ultrasound bath for 5 minutes.

The precipitated product was filtered off, washed with pentane (2×5 ml) and dried in vacuo, to afford the (pre) catalyst [(oTol)RuCl$_2$(PCy$_3$)(Ind)] (2) as a brown-red solid (257 mg, 53%). $^1$H NMR (200 MHz, CDCl$_3$): δ 8.70-8.25 (m, 2H), 7.60 (t, $^3$J(H,H) 6.8 Hz, 2H), 7.50-7.25 (m, 6H), 7.20-6.20 (m, 8H), 4.45-4.05 (m, 2H), 4.02-3.50 (m, 2H), 2.77-2.52 (m, 3H), 2.17-1.98 (m, 3H), 1.95-1.68 (bs, 3H), 1.67-0.57 (m, 30H). $^{13}$C NMR (125 MHz, CDCl$_3$): δ301.5, 222.3, 213.4 (d), 171.1, 160.5 (d), 147.3, 145.9, 145.5, 142.8, 141.1, 140.9, 140.3, 139.7, 139.1, 138.0, 137.8, 137.1, 136.6, 135.2, 134.5, 134.1, 131.7, 131.6, 131.0, 129.8, 129.4, 129.1, 128.8, 128.8, 128.6, 128.4, 128.2, 127.9, 127.7, 127.5, 126.6, 126.4, 126.1, 125.8, 124.9, 123.9, 123.8, 122.7, 117.8, 117.5, 116.6, 116.4, 103.0, 95.9, 92.7, 57.8, 53.2, 53.2, 51.1, 46.0, 38.2, 38.1, 34.1, 34.0, 33.8, 33.8, 30.6, 30.3, 29.1, 29.0, 28.8, 27.9, 27.8, 27.7, 27.6, 27.5, 26.8, 26.3, 26.2, 25.4, 22.3, 19.7, 19.6, 19.0, 18.4, 14.0. $^{31}$P NMR (80 MHz, toluene-d$_8$): δ 21.4, 21.3, 19.1, 15.9. IR (KBr): v3436 w, 3052 w, 2923 ss, 2847 s, 1494 s, 1438 s, 1425 s, 1270 s, 755 s, 735 m, 721 m, 697 m. Elemental analysis for C$_{50}$H$_{61}$N$_2$Cl$_2$PRu: calculated: C, 67.25; H, 6.89; N, 3.14; Cl 7.94. Found: C, 67.33; H, 6.90; N, 3.03; Cl, 7.91.

Example II:

Synthesis of the (Pre)Catalyst [(oTol)RuCl$_2$(Py)(Ind)] (Formula 3)

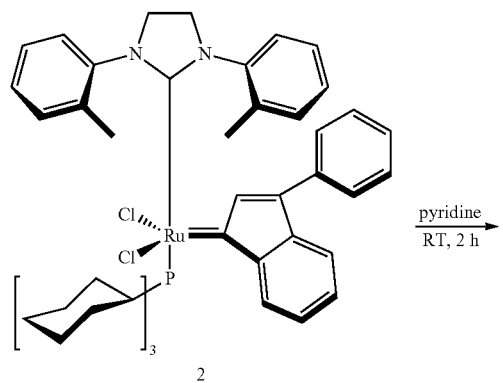

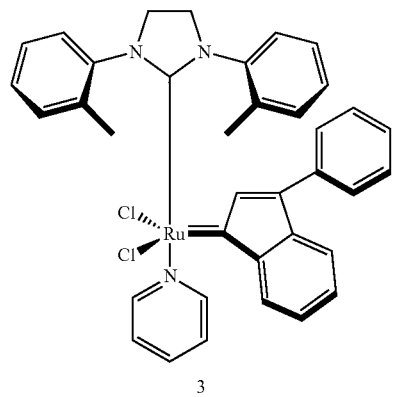

Using protective argon atmosphere, 100 mg of the solid (pre)catalyst [(oTol)RuCl$_2$(PCy$_3$)(Ind)] (2) were placed in the Schlenk flask, followed by adding dry, deoxygenated pyridine (0.9 ml). The reaction mixture was stirred at room temperature for 1 hour. From that moment on, all further operations were carried out without using protective argon atmosphere. n-Pentane was added to the reaction mixture (4 ml), the brown suspension was stirred at room temperature for another hour. The formed precipitate was filtered off, washed with n-pentane (2×4 ml) and dried in vacuo. The brown solid was dissolved in CH$_2$Cl$_2$ (3 ml), n-pentane (6 ml) was added in such a manner to avoid mixing with CH$_2$Cl$_2$; then the solution was left at a temperature of 4° C. for 12 hours; after that the solution was decanted, and the product was washed with n-pentane (2×4 ml) and dried in vacuo, to afford the (pre)catalyst [(oTol)RuCl$_2$(Py)(Ind)] (3) as a brown solid (60 mg, 78%). $^1$H NMR (200 MHz, C$_6$D$_6$): δ 9.45-9.20 (m, 1H), 8.60-8.42 (m, 2H), 8.38 (d, $^3$J(H, H) 7.0 Hz, 1H), 7.90-7.50 (m, 4H), 7.50-7.12 (m, 5H), 7.12-6.30 (m, 8H), 6.25-6.04 (m, 2H), 3.80-3.44 (m, 2H), 3.19-2.96 (m, 1H), 2.96-2.72 (m, 2H), 2.16 (s, 3H), 2.00-1.76 (m, 3H).

Example III

Synthesis of the (Pre)Catalyst [(oTol)RuCl$_2$(PPh$_3$)(Ind)] (Formula 4)

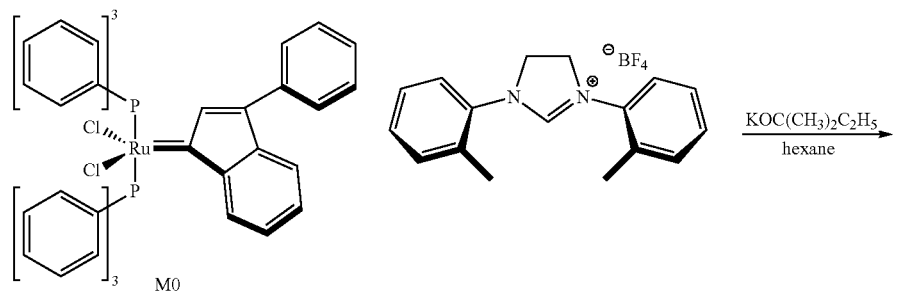

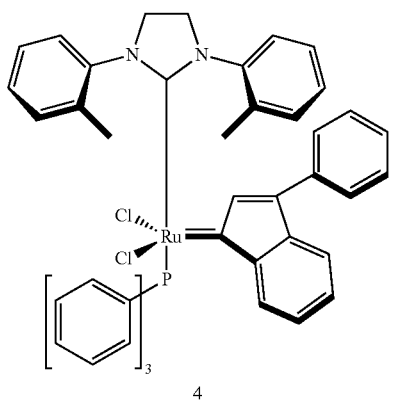

4

Using protective argon atmosphere, a solution of potassium tert-pentanolate (1.7 M in toluene, 1.33 ml, 2.26 mmol) was added to a flask containing the suspension of 763 mg (2.26 mmol) of 1,3-di-o-tolyl-4,5-dihydro-3H-imidazole tetrafluoroborate (the NHC salt) in dry and deoxygenated n-hexane (20 ml). The contents of the flask was stirred at room temperature for 20 minutes. After adding 1.0 g (1.13 mmol) of the (pre)catalyst (M0), the reaction mixture was heated for 15 minutes at reflux. After cooling to room temperature (from that moment on, all further operations were carried out without using protective argon atmosphere), the solvent was removed in vacuo, and the residue was chromatographed over silica gel, using 20% of ethyl acetate in cyclohexane as an eluent. Then the solvents were distilled off in vacuo and the product was washed with n-pentane to afford the (pre)catalyst [(oTol)RuCl$_2$(PPh$_3$)(Ind)] (4) (0.45 g, 46%) in the form of dark-red solid. $^1$H NMR (500 MHz, CDCl$_3$) δ: 8.33-8.13 (m, 2H), 7.69-6.46 (m, 31H), 4.40-4.24 (m, 2H), 3.91-3.64 (m, 2H), 2.79-2.75 (m, 3H), 1.85-1.60 (bs, 3H).

Example IV:

Synthesis of the (Pre)Catalyst [(IMoTol)RuCl$_2$(PCy$_3$)(Ind)] (Formula 5)

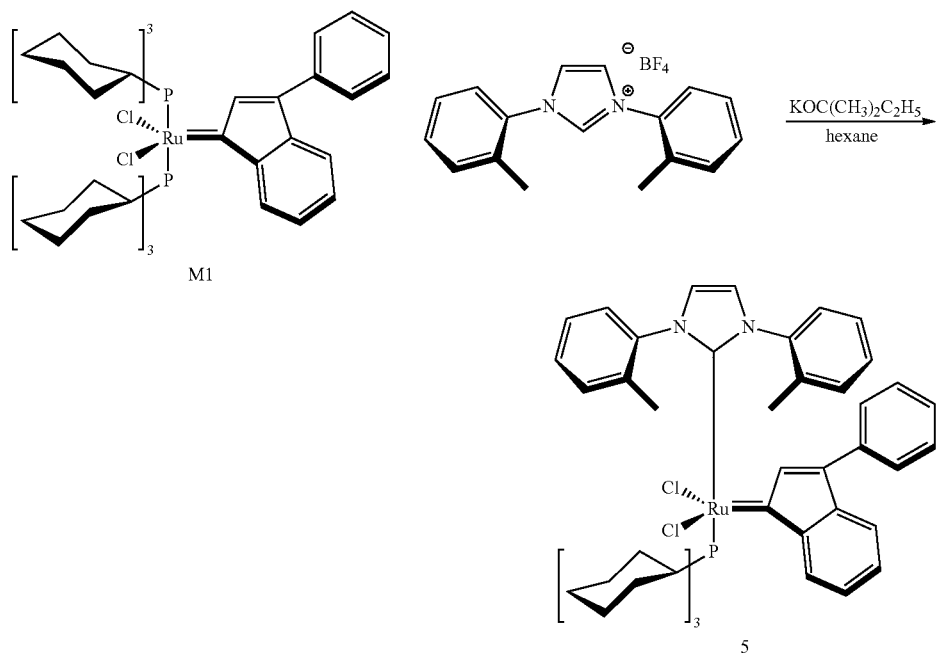

5

Using protective argon atmosphere, a solution of potassium tert-pentanolate (1.7 M in toluene, 0.89 ml, 1.52 mmol) was added to a suspension of 510 mg (1.52 mmol) of 1,3-di-o-tolyl-4,5-dihydro-3H-imidazole tetrafluoroborane (the NHC salt) in dry and deoxygenated n-hexane (20 ml) in a flask. The contents of the flask was stirred at room temperature for 20 minutes. After adding 1.0 g (1.08 mmol) of the (pre)catalyst (M1), the reaction mixture was heated for 15 minutes at reflux. After cooling to room temperature (from that moment on, all further operations were carried out without using protective argon atmosphere), the solvent was removed in vacuo, and the residue was chromatographed over silica gel, using 20% of ethyl acetate in cyclohexane as an eluent. Then the solvents were distilled off in vacuo and the product was washed with n-pentane to afford the (pre)catalyst [(IMoTol)RuCl$_2$(PCy$_3$)(Ind)] (5) (0.73 g, 76%) in the form of dark-red solid. $^1$H NMR (500 MHz, CDCl$_3$) δ: 8.48-8.21 (m, 2H), 7.71-6.57 (m, 18H), 2.67-2.61 (m, 3H), 2.07-1.99 (m, 3H), 1.86-0.78 (m, 33H). $^{13}$C NMR (75.4 MHz, CDCl$_3$) δ: 142.6, 141.8, 140.7, 139.1, 138.7, 138.4, 138.2, 137.9 (d), 136.7, 136.6, 134.1, 133.2, 131.5, 130.4, 129.7, 129.6, 129.4, 129.3, 129.0, 128.8, 128.7, 128.3, 128.2, 128.1, 128.0, 127.6, 127.4, 127.3, 127.2, 126.4, 126.3, 125.5, 124.4, 123.7, 123.5, 122.7, 116.7, 116.6, 34.2, 34.1, 33.8, 33.7, 29.3, 29.2, 28.9 (d), 27.9 (d), 27.8, 27.7, 27.6, 27.5, 27.4, 26.9, 26.8, 26.4, 26.3, 25.6, 22.3, 19.2, 18.9, 18.3, 14.1.

Example V:

Synthesis of the (Pre)Catalyst [(pXyl)RuCl$_2$(PCy$_3$)(Ind)] (Formula 6)

Using protective argon atmosphere, a solution of potassium tert-pentanolate (1.7 M in toluene, 0.3 ml, 0.51 mmol) was added to a suspension of 181 mg (0.5 mmol) of 1,3-di-(2,5-di-methylphenyl)-4,5-dihydro-3H-imidazole tetrafluoroborate (the NHC salt) in dry and deoxygenated n-hexane (25 ml) in a Schlenk flask. The contents of the flask was stirred at room temperature for 20 minutes. After adding 151 mg (0.165 mmol) of the (pre)catalyst (M1), the reaction mixture was heated for 45 minutes at reflux. After cooling to room temperature (from that moment on, all further operations were carried out without using protective argon atmosphere), the solvent was removed in vacuo, and the residue was chromatographed over silica gel, using 5% of ethyl acetate in cyclohexane as an eluent. Then the solvents were removed in vacuo to yield the product as a film, which was dissolved in n-hexane (15 ml) and sublimation drying was carried out to afford the (pre)catalyst [(pXyl)RuCl$_2$(PCy$_3$)(Ind)] (6) (72 mg, 48%) in the form of dark-red solid. $^1$H NMR (500 MHz, CDCl$_3$) δ: 8.67-7.85 (m, 1H) 7.80-6.25 (m, 15H), 4.60-3.30 (m, 4H), 3.00-0.22 (m, 45H).

Example VI:

Synthesis of the Hoveyda-Type (Pre)Catalyst [(oTol)RuCl$_2$(Hov)] (Formula 7)

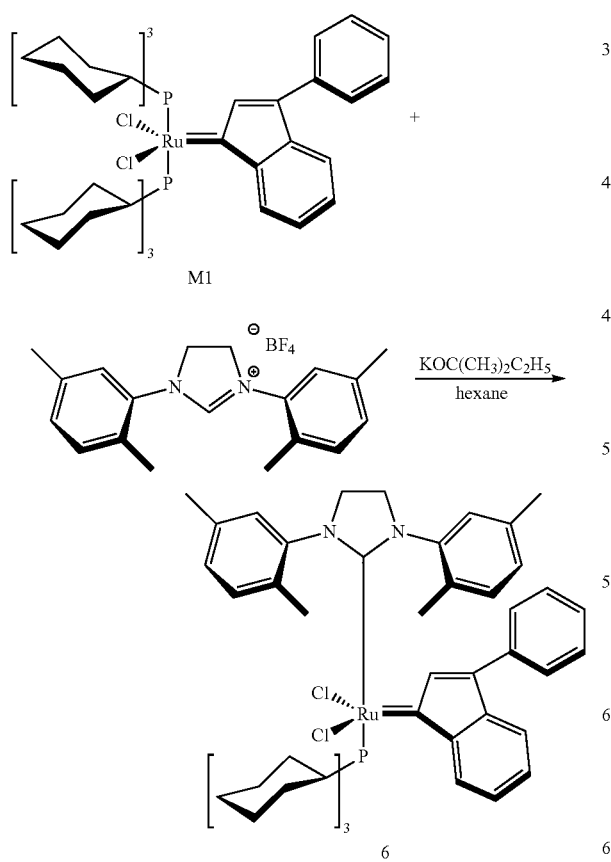

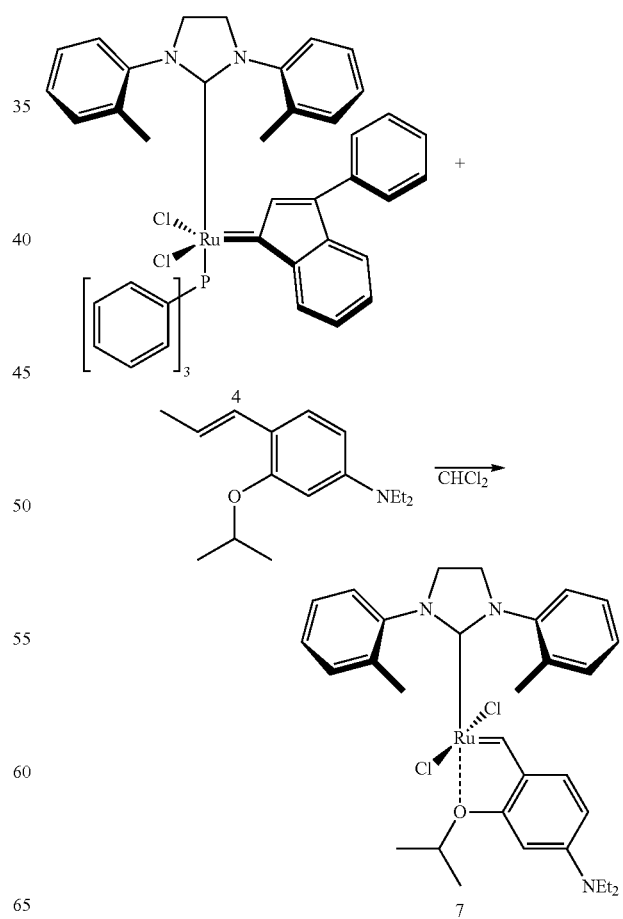

Using protective argon atmosphere, 50 mg (0.0572 mmol) of the solid (pre)catalyst [(oTol)RuCl$_2$(PPh$_3$)] (4) were placed in a Schlenk flask, followed by adding 2 ml of a solution of N,N-diethyl-3-isopropoxy-4-(prop-1-en-1-yl)aniline (cis and trans mixture) in chloroform (0.057M); the reaction mixture was heated for 45 minutes at reflux. After cooling to room temperature (from that moment on, all further operations were carried out without using protective argon atmosphere), the solvent was removed in vacuo, and the residue was chromatographed over silica gel, using 10% of ethyl acetate in cyclohexane as an eluent. Then the solvents were distilled off in vacuo and the product was washed with n-pentane, to afford the (pre)catalyst [(oTol)RuCl$_2$(Hov)] (7) (15.3 mg, 42%) in the form of a brown-green solid. $^1$H NMR (200 MHz, CDCl$_3$) δ: 15.60 (s, 1H) 8.80-8.45 (m, 1H), 8.10-7.15 (m, 8H), 6.57 (d, 1H), 6.07 (bs, 1H), 5.00-4.75 (m, 1H), 4.45-3.82 (m, 4H), 3.26 (dd, 4H), 2.80-2.30 (m, 6H), 1.83-0.80 (m, 12H).

Example VII:

Synthesis of the Hoveyda-Type (Pre)Catalyst [(oTol)RuCl$_2$(NHHov)] (Formula 8)

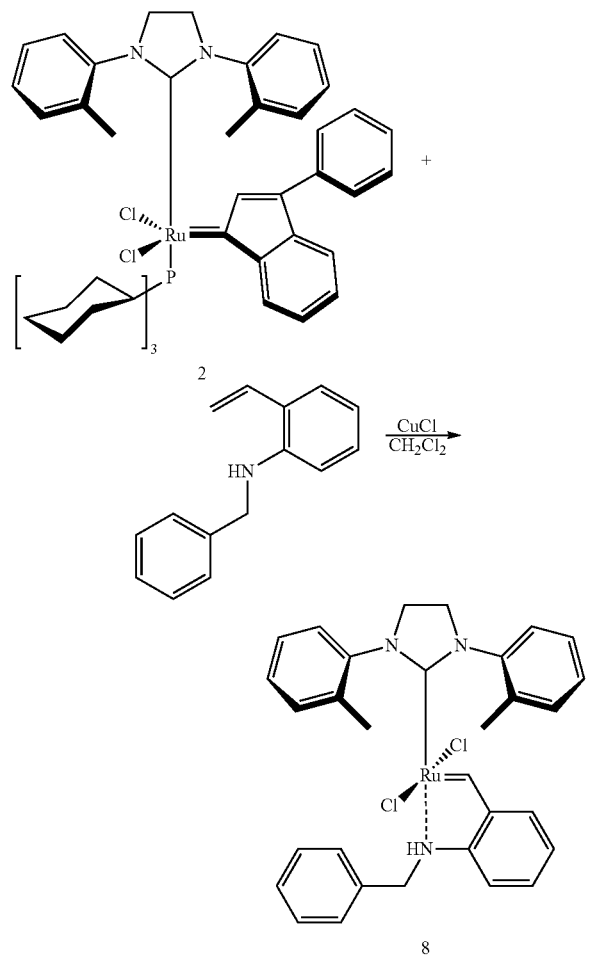

Using protective argon atmosphere, 100 mg (0.112 mmol) of the solid (pre)catalyst [(oTol)RuCl$_2$(PCy$_3$)] (2), 13.3 mg of copper(I) chloride (0.134 mmol) and 30.5 mg of (N-benzyl)-2-vinylaniline (0.146 mmol) were placed in a Schlenk flask.

The whole contents was dissolved in dry, deoxygenated dichloromethane (5 ml). The reaction mixture was heated at a temperature of 40° C. for an hour. From that moment on, all further operations were carried out without using protective argon atmosphere. After cooling to room temperature, the solvent was removed in vacuo. The residue was dissolved in ethyl acetate and filtered through a cotton pad. The obtained solution of the crude product was chromatographed over silica gel, using 10% of ethyl acetate in cyclohexane as an eluent. A noticeable decomposition of the (pre)catalyst occurred during the chromatography. The fractions containing the compound (8) were pooled and concentrated in vacuo. The product was precipitated from the dichloromethane/n-heptane system, to afford the (pre)catalyst [oTol)RuCl$_2$(NH-Hov)] (8) (5.0 mg, 7.2%) in the form of a bright green solid. IR (CH$_2$Cl$_2$): 3205, 3062, 3026, 2973, 2954, 2912, 2890, 1924, 1810, 1707, 1602, 1584, 1494, 1476, 1452, 1421, 1405, 1322, 1291, 1270, 1223, 1156, 1104, 1030, 986, 930, 866, 799, 762.754, 735, 721, 699, 654, 596, 550, 502, 459 cm$^{-1}$; MS (FD/FI) (m/z): [M+·] 719.1.

Example VIII:

$^1$H NMR Studies of Catalytic Activity in Cyclisation of dietyl di(allylmethyl)malonate

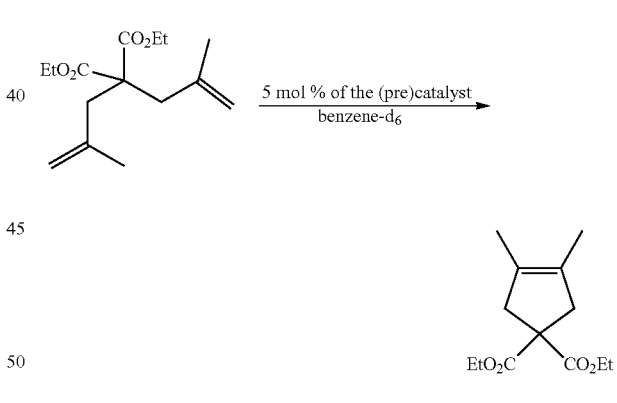

Using protective argon atmosphere, 16.1 mg (0.06 mmol) of diethyl di(allylmethyl)malonate was placed in the NMR tube, to which dry, deoxygenated benzene-d$_6$ (0.6 ml) was added; then 0.1 ml of a solution of the (pre)catalyst (0.03M, 0.003 mmol, 5 mol % of Ru) in dry, deoxygenated benzene-d$_6$ was added from a microsyringe. The NMR tube was closed with a septum, the time count started, the contents was stirred and placed in a thermostatted NMR apparatus (at a temperature of 40° C.), and the consecutive $^1$H NMR spectra were recorded. The activity of the commercially-available (pre) catalysts (A), (B) and (C) was investigated in an identical manner. Based on integration of signals originating from the substrate and the product, the conversions were determined, and the results were presented in FIG. 1, showing the reaction progress for cyclisation of diethyl di(allylmethyl)malonate in the presence of various catalysts.

Example IX:

GC Studies of Catalytic Activity in Cyclisation of N-tosyl-diallylamine

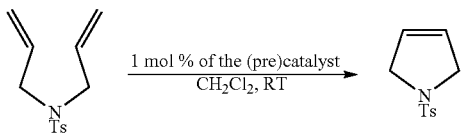

Figure 2:
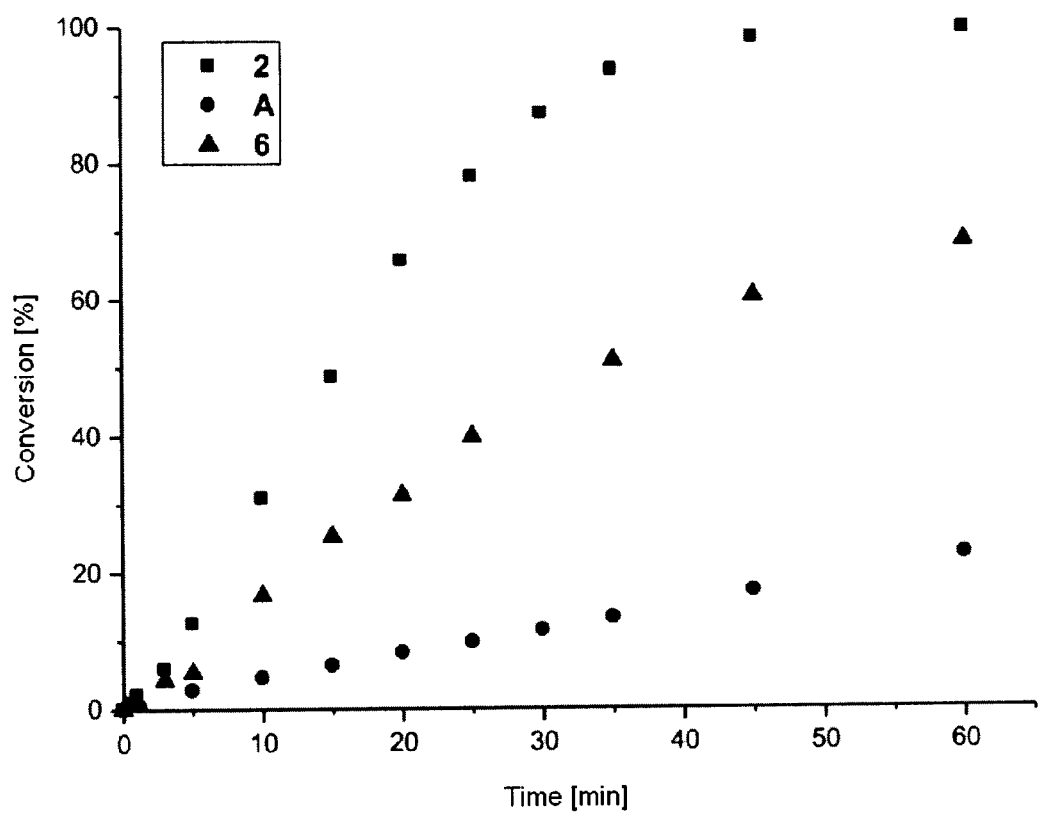
FIG. 2 shows the reaction progress for cyclisation of N-tosyl-diallylamine in the presence of various catalysts.
Figure 2:
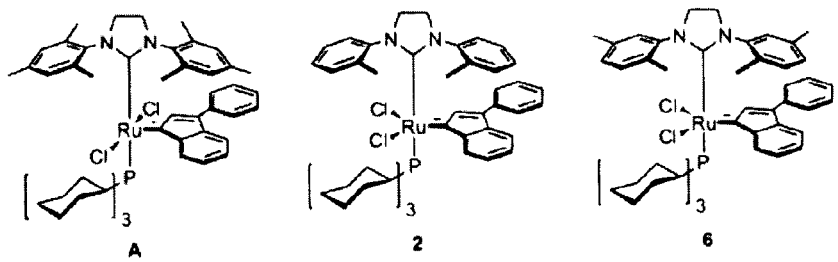

The reactions were carried out without using protective argon atmosphere, in the presence of air. 265 mg (1.05 mmol) of N-tosyl-diallylamine were placed in a flask, dichloromethane (5.25 ml) was added, followed by 0.0105 mmol of the (pre)catalyst (2) (1 mol % of Ru). At the same lo time, the time count started. The contents of the flask was stirred at room temperature for 60 minutes. At strictly defined time intervals, 0.1 ml aliquots of the reaction mixture were sampled using a microsyringe and immediately added to 1.0 ml of 0.002 M solution of 2-morpholinoethyl isocyanide in $CH_2Cl_2$. The so-obtained solutions were analysed by gas chromatography (GC). The activity of the (pre)catalyst (6) and the commercially available (pre)catalyst (A) was investigated in an identical manner. By integration of peaks originating from the substrate and the product, the conversions were determined, and the results were presented in FIG. 2, showing the reaction progress for cyclisation of N-tosyl-diallylamine in the presence of various catalysts.

Example X:

Studies on Stability of the (Pre)Catalysts

Using protective argon atmosphere, 0.0177 mmol of the (pre)catalyst (2) was placed in the NMR tube, to which dry, deoxygenated toluene-$d_8$ was added, followed by 0.1 ml of a solution of durene (11.9 mg, 0.0887 mmol of durene in 1.0 ml of dry, deoxygenated toluene-$d_8$) added from a micro-syringe. The NMR tube was closed with a septum, the time count started, the contents was stirred and placed in a thermostatted NMR apparatus (at a temperature of 22° C.), and the consecutive spectra $^1H$ NMR were recorded. The activity lo of the commercially-available (pre)catalysts was investigated in an identical manner (the tested (pre)catalyst (D) was taken from a freshly open package (Aldrich)). In the case of the (pre)catalyst (2), based on the ratio of the integrated signals in the range of δ 8.5-9.2 ppm to the integrated signal at δ 6.80 ppm originating from the internal standard (durene), the amount of the (pre)catalyst was calculated, and the results were shown in Table 1, presenting a percentage amount of the (pre)catalyst, that resisted decomposition after a given period of time.

In the case of the ruthenium complex (D), the percentage amount of the (pre)catalyst, that resisted decomposition after a given period of time, was determined basing on the ratio of integrated signal at δ 19.6 ppm to integrated signal at δ 6.8 ppm originating from the internal standard

TABLE 1

| Time [h] | (Pre)catalyst (2) [%] | (Pre)catalyst (D) [%] |
| --- | --- | --- |
| 50 | 96 | 78 |
| 330 | 21 | 0 |

Example XI:

The catalytic activity tests were performed using various substrates.

General Procedures for Carrying out the Catalytic Activity Test

Procedure A: Using protective argon atmosphere, 16.1 mg (0.06 mmol) of diethyl di(allylmethyl)malonate were placed in an NMR tube, to which dry, deoxygenated benzene-$d_6$ (0.6 ml) was added, followed by 0.1 ml of the solution of the lo (pre)catalyst (0.03M, 0.003 mmol, 5 mol % of Ru) in dry, deoxygenated benzene-$d_6$, added from a microsyringe. The NMR tube was closed with a septum, the contents was stirred and placed in a thermostatted NMR apparatus (at a temperature of 40° C.), and the $^1H$ NMR was registered after a specified is period of time. Based on the integrated signals originating from the substrate and the product, the conversions were calculated, and the results were presented in Table 2 below.

Procedure B: Using protective argon atmosphere, the substrate (0.5 mmol), dry deoxygenated solvent (5 ml; dichloromethane for the reactions carried out at room temperature, or toluene for the reactions carried out at a temperature of 60° C., respectively), and methyl acrylate (1 mmol, 2 equivalents) were placed in a Schlenk flask, in the case of cross metathesis (CM). The reaction mixture was warmed to the planned temperature, followed by adding an appropriate amount of the (pre)catalyst. The resulting solution was stirred at planned temperature for a period of time of from 1 to 24 hours. From that moment on, all further operations were carried out without using protective argon atmosphere. The reaction mixture was cooled down to room temperature, concentrated in vacuo, and the obtained residue was chromatographed over silica gel, using ethyl acetate in cyclohexane as an eluent. The test results are presented in the following Tables 3 and 4.

TABLE 2

Diene RCM substrate → cyclopentene product (via (pre)catalyst, benzene-$d_6$)

| (Pre)catalyst | mol % | Temp. | Time [h] | Conversion [%] |
|---|---|---|---|---|
| D (o-tolyl SIMes–type NHC, PCy$_3$, Cl$_2$Ru=CHPh benzylidene) | 5.0 | 40 | 1 | 45 |
| 2 (o-tolyl SIMes–type NHC, PCy$_3$, Cl$_2$Ru= 3-phenylindenylidene) | 5.0 | 40 | 11 | 75 |
| A (mesityl SIMes NHC, PCy$_3$, Cl$_2$Ru= 3-phenylindenylidene) | 5.0 | 40 | 1 | 8 |

TABLE 3

| (Pre)catalyst | | mol % | Temp. | Time [h] | Yield [%] |
|---|---|---|---|---|---|
| D | Ru complex with bis(o-tolyl)imidazolidine NHC, two Cl, PCy₃, benzylidene | 0.5 | 60 | 1 | 69 |
| 2 | Ru complex with bis(o-tolyl)imidazolidine NHC, two Cl, PCy₃, 3-phenylindenylidene | 0.5 | 60 | 1 | 98 |
| A | Ru complex with SIMes NHC, two Cl, PCy₃, 3-phenylindenylidene | 0.5 | 60 | 20 | 61 |

TABLE 4

| Substrate | Product | mol % | Temp. | Time [h] | Yield [%] |
|---|---|---|---|---|---|
| | | | (Solvent) | | |
| 4-allyl-5-BnO-3-Ts-1-Ts-indole | methyl (E)-4-(5-BnO-3-Ts-1-Ts-indol-4-yl)but-2-enoate | 2 × 5.0 | 60 | 20 | 45 |
| | | | (toluene) | | |
| TBDMSO-(CH2)3-CH=CH2 | TBDMSO-(CH2)3-CH=CH-CO2Me | 2.0 | 60 | 1 | 91 |
| | | | (toluene) | | |
| 2-methyl-N-Ts-N-(but-3-enyl)allylamine | 5-methyl-1-Ts-1,2,3,6-tetrahydropyridine | 0.5 | 22 | 18 | 74 |
| | | | (toluene) | | |
| allyl (1,1-diphenylprop-2-ynyl) ether | 2,2-diphenyl-3-vinyl-2,5-dihydrofuran | 2.0 | 22 | 3 | 99 |
| | | | (dichloromethane) | | |

Example XII:

The Reaction of Cyclisation of Diethyl di(allylmethyl)malonate with Continuous Addition of the (Pre)Catalyst.

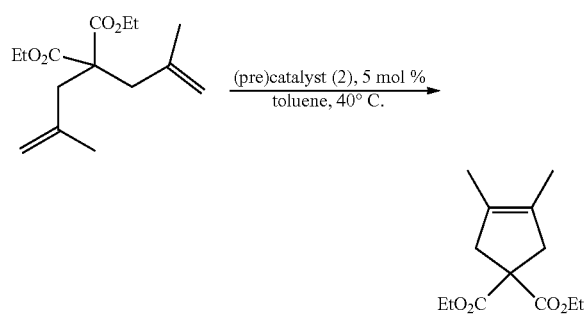

A solution of the (pre)catalyst [(oTol)RuCl$_2$(PCy$_3$)(Ind)] (2) (34 mg, 5 mol%) in dry toluene (3.3 ml) was added over 3 hours using a syringe pump (at a constant rate of 1.1 ml/h), to the solution of diethyl di(allylmethyl)malonate (205 mg, 0.76 mmol) in toluene (7.5 ml). The reaction was lo carried out at a temperature of 40° C. After 4 hours, the substrate conversion was 96%, as determined based on the GC analysis.

Example XIII:

The Reaction of Isomerisation of cis-1,4-diacetoxy-2-butene

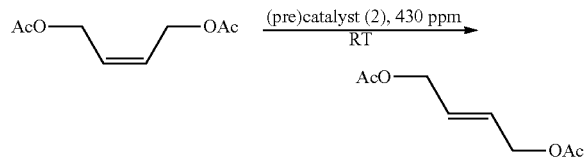

The reactions were carried out without using protective argon atmosphere, in the presence of air, and without using any solvent. 5.0 mg (0.00723 mmol, 430 ppm) of the (pre)catalyst [(oTol)RuCl$_2$(PCy$_3$)(Ind)] (2) were weighed into a small vial, followed by adding 2.22 g of cis-1,4-diacetoxy-2-butene (12.9 mmol, 2300 equivalents). The reaction mixture was stirred at room temperature. After 4 hours, the substrate conversion was 60%, as determined based on the GC analysis.

Example XIV:

The Reaction of Homometathesis of 1-dodecene

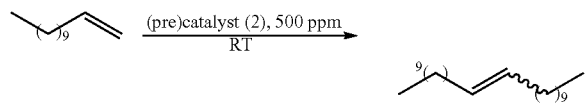

The reactions were carried out without using protective argon atmosphere, in the presence of air, and without using any solvent. 7.3 mg (0.00817 mmol, 500 ppm) of the (pre)catalyst [(oTol)RuCl$_2$(PCy$_3$)(Ind)] (2) were weighed into a small vial, followed by adding 2.75 g of 1-dodecene (16.3 mmol, 2000 equivalents). The reaction mixture was lo stirred at room temperature. After 20 hours, the substrate conversion was 66%, as determined based on the GC analysis.

Example XV:

An example of using novel complexes of ruthenium according to the invention as (pre)catalysts of the ROMP-type polymerisation.

A) Preparation of polydicyclopentadiene (pDCPD):

The reactions were carried out without using protective argon atmosphere, in the presence of air. 5 mg (0.00723 mmol) of the (pre)catalyst [(oTol)RuCl$_2$(Py)(Ind)] (3) were weighed into a small vial, followed by adding a minimum volume of dichloromethane in order to dissolve the complex of ruthenium. This was followed by adding 287 mg of dicyclopentadiene (2.17 mmol, 300 equivalents). The reaction mixture was left at room temperature for 24 hours. Polydicyclopentadiene was obtained as an elastic brown solid.

B) Otrzymywanie polynorbornenu (pNB):

Using protective argon atmosphere, 2.5 mg of the solid (pre)catalyst [(oTol)RuCl$_2$(Py)(Ind)] (3) were placed in the Schlenk flask #1. Using protective argon atmosphere, 102 mg of norbornene (1.08 mmol, 300 equivalents) were placed in the Schlenk flask #2. Then dry and deoxygenated dichloromethane (5 ml in each case) was added to both Schlenk flasks. The monomer solution was added to the Schlenk flask #1. The resulting reaction mixture was stirred at room temperature for 12 hours. From that moment on, all further operations were carried out without using protective argon atmosphere. The reaction mixture was concentrated in vacuo, followed by adding cooled methanol (10 ml). The precipitated solid was separated by filtration and dried in vacuo using a vacuum pump. Polynorbornene was obtained as a white solid.

SUMMARY

These examples show that the metal complexes according to the invention may be successfully used as (pre)catalysts in the ROMP-type polymerisation reactions. Based on the above-presented embodiments of the invention, one may conclude that, compared to the complexes of metals already known from the state of the art, the complexes of the formula (1) according to the invention demonstrate a higher catalytic activity. Besides, the complexes of the formula (1) according to the invention are stable at elevated temperature and may be stored and used without protective gas atmosphere.

The invention claimed is:

1. A metal complex of the formula (1):

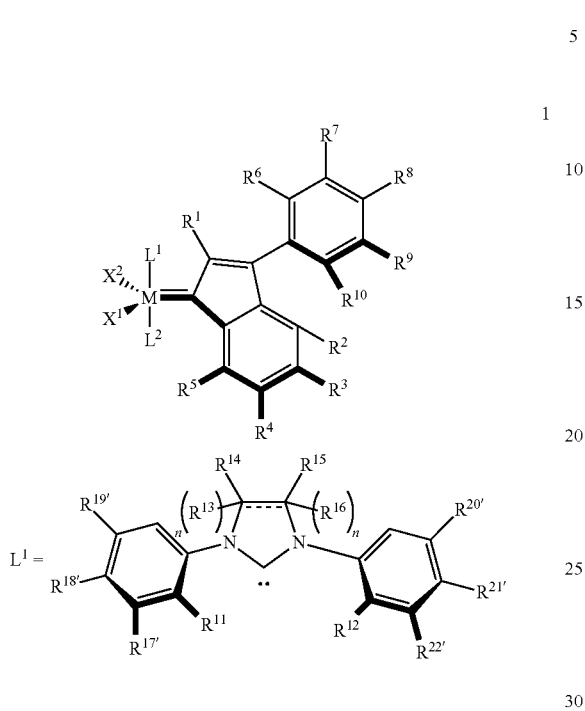

wherein:

M is ruthenium;

$L^1$ is a N-heterocyclic carbene lignad, where $R^{11}$, and $R^{12}$ are methyl, each $R^{17'}$, $R^{18'}$, $R^{19'}$, $R^{20'}$, $R^{21'}$, and $R^{22'}$ are independently hydrogen, or methyl;

each $R^{13}$, $R^{14}$, $R^{15}$, and $R^{16}$ are independently hydrogen or methyl;

n is 0 or 1;

$L^2$ is a neutral ligand;

$X^1$ and $X^2$ are independently an anionic ligand;

$R^1$, $R^2$, $R^3$, $R^4$, $R^5$, $R^6$, $R^7$, $R^8$, $R^9$, and $R^{10}$ are independently hydrogen, halogen, or $C_1$-$C_6$ alkoxy.

2. The complex according to claim 1, wherein $L^2$ is described by the formula $P(R^{17})(R^{18})(R^{19})$, where $R^{17}$, $R^{18}$, and $R^{19}$ are independently $C_1$-$C_{12}$ alkyl, $C_1$-$C_{12}$ alkoxy, $C_3$-$C_{12}$ cycloalkyl, $C_5$-$C_{12}$ aryl, $C_5$-$C_{12}$ aryloxy, or $C_5$-$C_{12}$ heteroaryl, where two substituents selected from $R^{17}$, $R^{18}$ and $R^{19}$ may be joined together to from a cyclic or polycyclic system; or a nitrogen-containing heterocycle, optionally substituted with at least one $C_1$-$C_{12}$ alkyl, $C_1$-$C_{12}$ perhalo-alkyl, $C_1$-$C_{12}$ alkoxy, amino, cyano, alkoxy, or halogen(s);

$X^1$ and $X^2$ are chloro.

3. The complex according to claim 1, of the structural formula selected from the following formulae (2), (3), (4), (5) and (6):

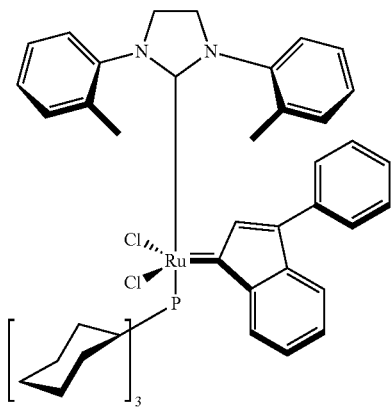

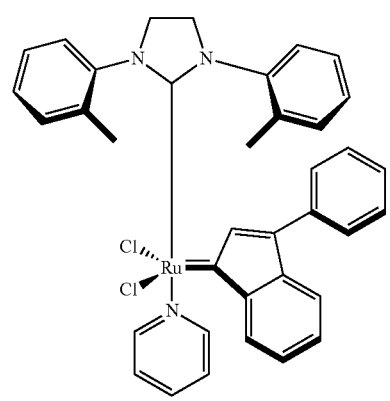

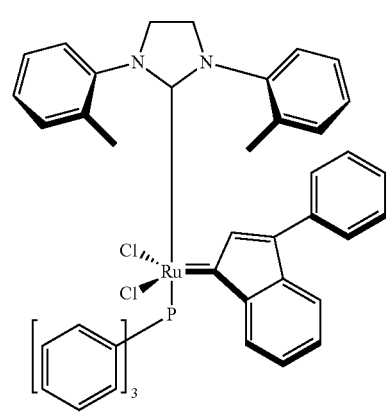

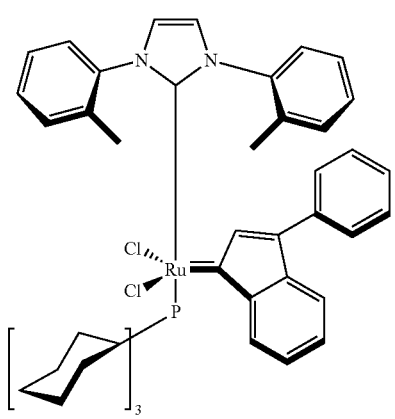

-continued

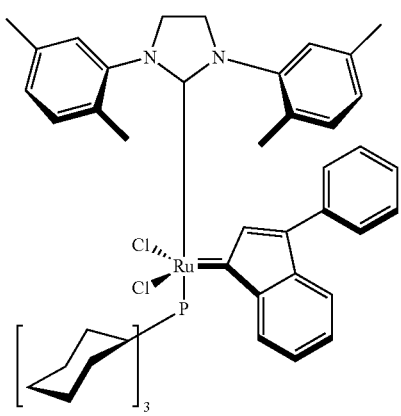

4. A process of using one or more complexes of ruthenium of the formula (1), as defined in claim 1, as a (pre)catalyst in the olefin metathesis reaction, comprising contacting the complex of formula (I) with an olefin.

5. The process according to claim 4, wherein the ruthenium complex of the formula (1) is used as a (pre)catalyst in the ring-closing metathesis (RCM), homometathesis, cross metathesis (CM), "alkene-alkene" (ene-yne) type metathesis, isomerisation, or ROMP-type polymerisation reactions.

6. The process according to claim 4, wherein the ruthenium complex of the formula (1) is used as a (pre)catalyst in the metathetic polymerisation reaction with opening of ring of dicyclopentadiene or norbornene.

7. The process according to claim 4, wherein a solution of the (pre)catalyst of the formula (1) is added to a reaction mixture containing the olefin in a period of from 1 minute to 24 h.

8. The process according to claim 7, wherein the (pre)catalyst is prepared in a solvent that is the same solvent in which the metathesis reaction is carried out.

9. The process according to claim 4, wherein the metathesis reaction is carried out without using any solvent.

10. The complex of claim 2 wherein the nitrogen-containing heterocycle is 1,2,3-triazole, 1,3,4-triazole, pyridine, 4-(N,N-dimethylamino)pyridine (DMAP), piperidine, morpholine, thiomorpholine, pyridazine, pyrimidine, pyrazine, piperazine, 1,2,3-triazine 1,2,4-triazine, 1,3,5-triazine, quinoline, isoquinoline, quinuclidine, phthalazine, indoline, thiazole, benzothiazole, benzimidazole, purine, 1,8-naphthyridine, quinoxaline, pteridine, carbazole, phenazine, carboline, isothiazole, tetrazole, quinine, cinchonine, quinidine, cinchonidine, 1,8-diazabicyclo[5.4.0]undec-7-ene (DBU), 1,4-diazabicyclo[2.2.2]octane (DABCO), 1,5-diazabicyclo[4.3.0]non-5-ene (DBN), phenanthroline, or bipyridyl (as a single isomer or as a mixture of isomers).

* * * * *